United States Patent
Ramachandran et al.

(10) Patent No.: US 10,820,830 B2
(45) Date of Patent: Nov. 3, 2020

(54) REFERENCE MARKERS FOR LAUNCH POINT IDENTIFICATION IN OPTICAL SHAPE SENSING SYSTEMS

(75) Inventors: Bharat Ramachandran, Morganville, NJ (US); Raymond Chan, San Diego, CA (US); Robert Manzke, Sleepy Hollow, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 339 days.

(21) Appl. No.: 13/981,631

(22) PCT Filed: Jan. 24, 2012

(86) PCT No.: PCT/IB2012/050321
§ 371 (c)(1),
(2), (4) Date: Jul. 25, 2013

(87) PCT Pub. No.: WO2012/101575
PCT Pub. Date: Aug. 2, 2012

(65) Prior Publication Data
US 2013/0317356 A1  Nov. 28, 2013

Related U.S. Application Data

(60) Provisional application No. 61/437,160, filed on Jan. 28, 2011.

(51) Int. Cl.
*A61B 5/06* (2006.01)
*A61B 34/20* (2016.01)

(52) U.S. Cl.
CPC .............. *A61B 5/064* (2013.01); *A61B 34/20* (2016.02); *A61B 2034/2061* (2016.02)

(58) Field of Classification Search
CPC ........ A61B 19/5244; A61B 2019/5261; A61B 5/064
See application file for complete search history.

(56) References Cited

U.S. PATENT DOCUMENTS

| | | | |
|---|---|---|---|
| 5,588,430 A * | 12/1996 | Bova | A61B 6/035 378/204 |
| 5,987,960 A | 11/1999 | Messner et al. | |
| 7,043,961 B2 | 5/2006 | Pandey et al. | |
| 8,439,826 B2 | 5/2013 | Onoda et al. | |

(Continued)

FOREIGN PATENT DOCUMENTS

| | | |
|---|---|---|
| JP | 09166411 A | 6/1997 |
| JP | 2000081302 A | 3/2000 |

(Continued)

*Primary Examiner* — Amelie R Davis

(57) ABSTRACT

An optical shape sensing system employing an optical fiber (20) and one or more reference markers (41). Each reference marker (41) has an identifiable reference tracking position within a reference coordinate system (42). The optical fiber (20) has a reconstruction launch point (21) within the reference coordinate system (42) serving as a basis for an execution of a shape reconstruction of the optical fiber (20) within the reference coordinate system (42). The reconstruction launch point (21) of the optical fiber (20) has a known spatial relationship with each reference marker (41) to facilitate an identification of the reconstruction launch point (21) within the reference coordinate system (42).

19 Claims, 4 Drawing Sheets

(56) References Cited

U.S. PATENT DOCUMENTS

| | | | |
|---|---|---|---|
| 2002/0052546 A1 | 5/2002 | Frantz | |
| 2003/0002009 A1 | 11/2003 | Pandey et al. | |
| 2003/0209096 A1 | 11/2003 | Pandey et al. | |
| 2006/0241395 A1 | 10/2006 | Kruger et al. | |
| 2009/0137952 A1* | 5/2009 | Ramamurthy | A61B 5/06 604/95.01 |
| 2009/0169080 A1 | 7/2009 | Noordhoek | |
| 2010/0030063 A1 | 2/2010 | Lee et al. | |
| 2010/0063400 A1* | 3/2010 | Hall | A61B 6/12 600/466 |
| 2010/0210939 A1* | 8/2010 | Hartmann | A61B 19/5244 600/424 |
| 2011/0098533 A1* | 4/2011 | Onoda | A61B 1/0051 600/117 |

FOREIGN PATENT DOCUMENTS

| | | |
|---|---|---|
| JP | 2001169998 A | 6/2001 |
| WO | 0133165 A1 | 5/2001 |

\* cited by examiner

REFERENCE MARKERS FOR LAUNCH POINT IDENTIFICATION IN OPTICAL SHAPE SENSING SYSTEMS

CROSS-REFERENCE TO PRIOR APPLICATIONS

This application is the U.S. National Phase application under 35 U.S.C. § 371 of International Application Serial No. PCT/IB2012/050321, filed on Jan. 24, 2012, which claims the benefit of Application Ser. No. 61/437,160, filed on Jan. 28, 2011. These applications are hereby incorporated by reference herein.

FIELD OF THE INVENTION

The present invention generally relates to a shape reconstruction of optical fibers. The present invention specifically relates to a reliable identification of launch points for an accurate shape reconstruction of optical fibers.

BACKGROUND OF THE INVENTION

Optical shape sensing systems as known in the art have the ability to revolutionize and transform minimally-invasive surgical procedures performed in an interventional setting today due to the potential of optical shape sensing systems to display the shape of an optical fiber enclosed within a device like an endoscope, a catheter or a guidewire in a real-time manner. However, these optical fibers need to be launched from a known reference position for accurate shape reconstruction.

In particular, shape reconstruction of the optic fiber may be performed in an integrative manner in according with the following equation $\vec{r}_{i+1} = \vec{r}_i + \Delta \vec{s}_{i+1}$, where $\vec{r}_i$ is the position vector to the first spatial element along the shape sensing optical fiber and $\Delta \vec{s}_{i+1}$ is the reconstructed incremental step vector derived from the actual strain measurement of the optical fiber. For shape reconstruction, it may be assumed $\vec{r}_0$ to be $(0,0,0)^T$. Obviously any error acquired in the reconstructed incremental step vector $\Delta \vec{s}_{i+1}$, for example due to measurement noise, will propagate forward and impact the shape reconstruction accuracy of the optical fiber.

SUMMARY OF THE INVENTION

The knowledge of the exact launching point of the optical fiber is therefore crucial for accurate shape reconstruction. The present invention provides an optical shape sensing system for identifying of one or more launching points by making use of reference markers (e.g., electromagnetic reference markers, optical reference markers, radioactive reference markers, etc.).

Furthermore, in current optical shape sensing systems, if there is a change in the position of the launching point, the shape reconstruction would fail. The optical shape sensing system of present invention, for the first time, allows for the detection of changes in the position of the launching point and its subsequent compensation.

Additionally, by combining different tracking technologies like optical shape sensing, electromagnetic tracking and optical tracking, the optical shape sensing system of the present invention overcomes the inherent limitations of these technologies. For example, the sensitivity of electromagnetic tracking to field distortions, line of sight limitations of optical tracking and current sensitivity of optical shape sensing to temperature and strain/vibration based fluctuations.

One form of the present invention is an optical shape sensing system employing an optical fiber and one or more reference markers. Each reference marker has one or both of an identifiable reference tracking position and an identifiable reference tracking orientation within a reference coordinate system. The optical fiber has a reconstruction launch point within the reference coordinate system serving as a basis for an execution of a shape reconstruction of the optical fiber within the reference coordinate system. The reconstruction launch point of the optical fiber has a known spatial relationship with each reference marker to facilitate an identification of the reconstruction launch point within the reference coordinate system.

A second form of the present invention is an optical shape sensing method involving an identification of one or both of an identifiable reference tracking position and an identifiable reference tracking orientation for each reference marker within a reference coordinate system and an identification of a reconstruction launch point of an optical fiber within the reference coordinate system, the reconstruction launch point of the optical fiber having a known spatial relationship with each reference marker to enable the identification of the reconstruction launch point within the reference coordinate system. The optical shape sensing method further involves an execution of a shape reconstruction of the optical fiber within the reference coordinate system based on the identification of the reconstruction launch point within the reference coordinate system.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

BREIF DESCRIPTION OF THE DRAWINGS

DETAILED DESCRIPTION OF THE PREFERRED EMBODIMENTS

Figure 1:
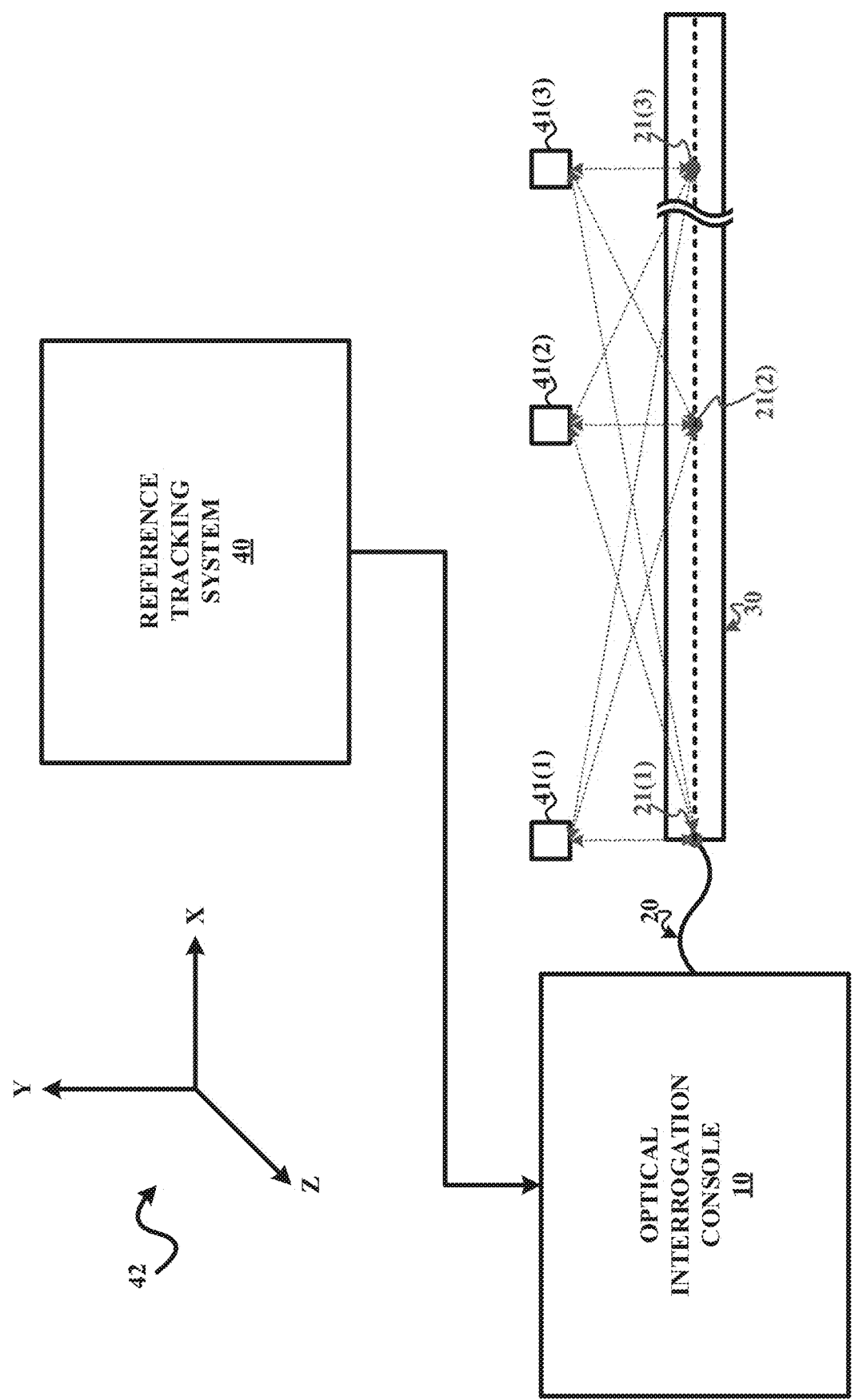
FIG. 1 illustrates an exemplary embodiment of an optical shape sensing system in accordance with present invention.

As shown in FIG. 1, an optical shape sensing system of the present invention employs an optical fiber 20 embedded within an elongated device 30.

In practice, optical fiber 20 may be any type of optical fiber suitable for optically tracking elongated device 30. Examples of optical fiber 20 include, but are not limited to, a flexible optically transparent glass or plastic fiber incorporating an array of fiber Bragg gratings integrated along a length of the fiber as known in the art, and a flexible optically transparent glass or plastic fiber having naturally variations in its optic refractive index occurring along a length of the fiber as known in the art (e.g., a Rayleigh scattering based optical fiber). Optical fiber 20 may be a single core fiber or preferably, a multi-core fiber.

In practice, elongated device 30 may be any type of device suitable for embedding an optical fiber 20 therein for purposes of optically tracking elongated device 30. Examples of elongated device 30 include, but are not limited to, an endoscope, a catheter and a guidewire.

Still referring to FIG. 1, the system further employs an optical interrogation console 10 and a reference tracking system 40.

In practice, optical interrogation console 10 may be any device or system structurally configured for transmitting light to optical fiber 20 and receiving reflected light from optical fiber 20. In one embodiment, optical interrogation console 10 employs an optical Fourier domain reflectometer and other appropriate electronics/devices as known in the art.

In practice, reference tracking system 40 is broadly defined herein as any type of imaging guidance system employing reference markers 41 with each reference marker 41 having a reference tracking position and/or reference tracking orientation with a reference coordinate system 42.

In one embodiment, reference tracking system 40 is an electromagnetic tracking system employing an electromagnetic tracking console, a field generator and reference markers 41 in the form of sensor coils.

In a second embodiment, reference tracking system 40 is an optical tracking system employing an optical tracking console and reference markers 41 in the form of active light emitting diodes or passive spheres.

In a third embodiment, reference tracking system 40 is an imaging tracking system employing an imaging modality for imaging optical fiber 20 within reference coordinate system 42. Examples of an imaging tracking system known in the art include, but are not limited to, an X-ray system, a MRI system, a CT system, an US system, an IVUS system, a PET system, a SPECT system or a combination thereof.

In practice, the form of reference markers 41 are dependent upon the type of imaging tracking system. For example, reference markers 41 may be iodine based markers which are visible in X-ray images. By further example, reference markers 41 may be radioactive or radio-opaque marks which are identifiable in nuclear based imaging tracking systems (e.g., PET system or a SPECT system).

Optical interrogation console 10 further employs shape reconstruction algorithms as known in the art for reconstructing a shape of an entirety or a portion of optical fiber 20 relative to one or more reconstruction launch points, such as, for example, reconstruction launch points 21 shown in FIG. 1. Reconstruction launch point 21 (1) serves as a basis of a shape reconstruction of an entirety of a portion of optical fiber 20 embedded within elongated device 30 as known in the art, while launch points 21 (2) and 21 (3) serve as a basis of a shape reconstruction of different segments of the portion of optical fiber 20 embedded within elongated device 30 as known in the art.

The present invention is premised on a known spatial relationship (e.g., known distance and/or angular orientation) as indicated by the bi-directional arrows of one or more reference markers 41 to each reconstruction launch point 21 whereby an identification of the reference tracking positions and/or reference tracking orientations of the reference markers 41 within reference coordinate system 42 enables the identification of reconstruction launch point(s) 21 within reference coordinate system 42.

More particularly, in operation, reference tracking system 40 identifies a reference tracking position and/or reference tracking orientation of each reference marker 41 within reference coordinate system 42, which is utilized to identify one or more reconstruction launch points 21 for optical fiber 20 within reference coordinate system 42. Thereafter, optical interrogation console 10 executes a shape reconstruction of optical fiber 20 until the tracking procedure is complete or reference tracking system 40 communicates feedback to optical interrogation console 10 of a movement one or more reference markers 41 within reference coordinate system 42. If the latter, then reference tracking system re-identifies a new reference tracking position and/or reference tracking orientation of each reference marker 41 within reference coordinate system 42, which is utilized to re-identify one or more reconstruction launch points 21 for optical fiber 20 within the reference coordinate system 42. Thereafter, optical interrogation console 10 re-executes a shape reconstruction of optical fiber 20 until the tracking procedure is complete or reference tracking system 40 communicates feedback to optical interrogation console 10 of another movement of one or more reference markers 41 and optical fiber 20 within reference coordinate system 42.

In practice, for embodiments having multiple reconstruction launch points, a particular reconstruction launch point 21 may be selected by various means. For example, the reconstruction launch points 21 may be displayed whereby a user of the system may select one of the reconstruction launch points 21.

FIGS. 2-5 illustrate various embodiments of an optical shape sensing device in accordance with the present invention.

Figure 2:
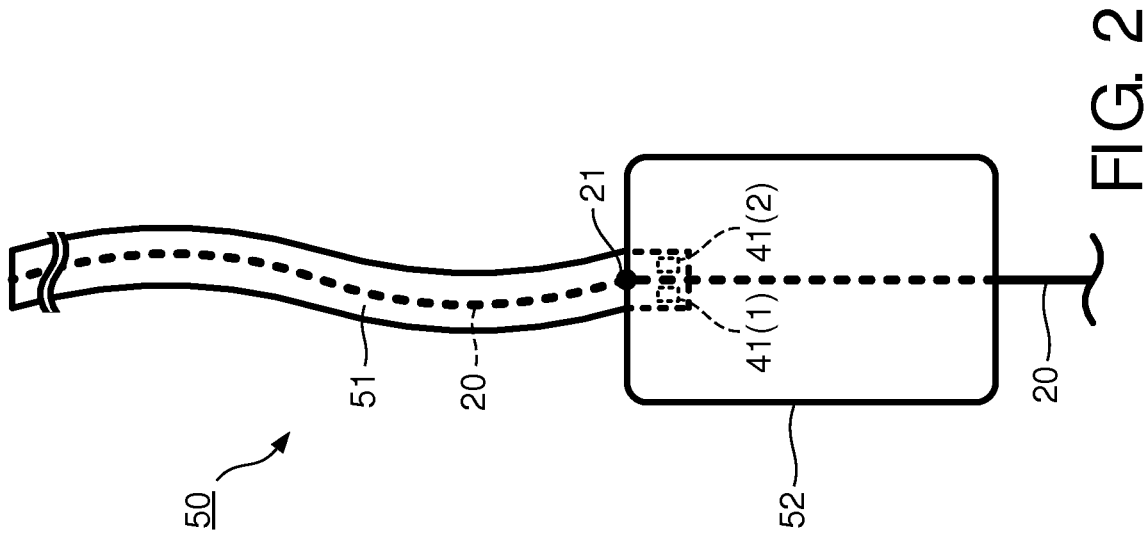

As shown in FIG. 2, an optical shape sensing device 50 employs an elongated device 51 and a handle 52 (e.g., a catheter and catheter handle) for optical fiber 20. In this embodiment, reference markers 41 are embedded in elongated device 51 as shown, and the spatial relationship of reference markers 41 and reconstruction launch point 21 is known.

Figure 3:
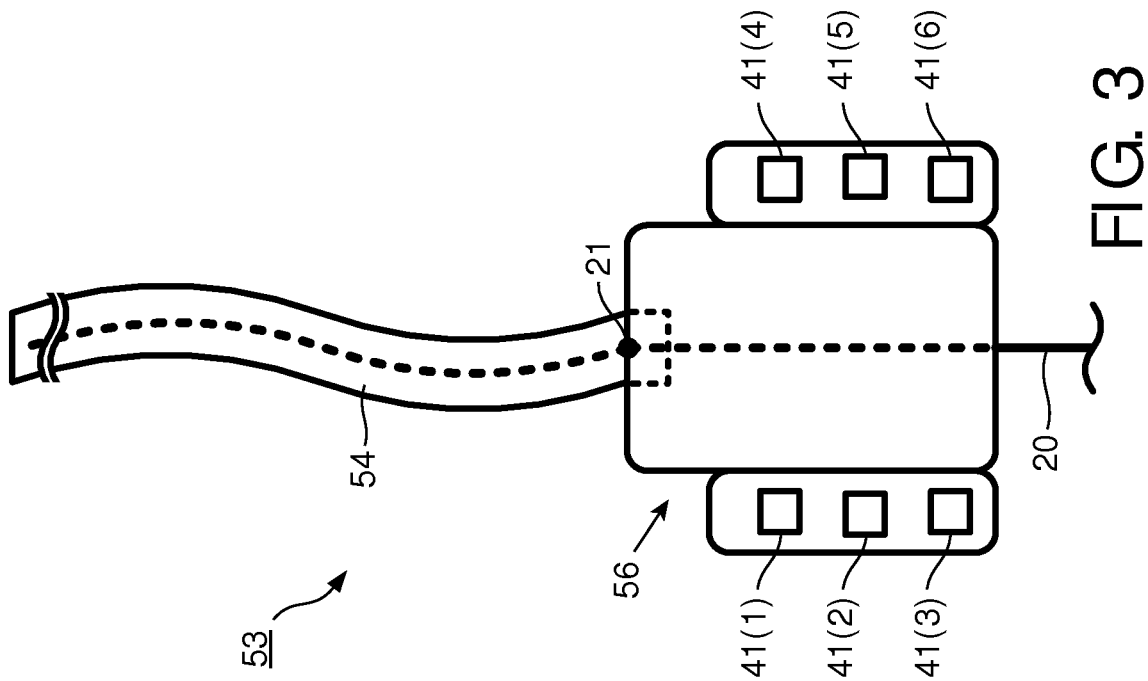
FIGS. 2-5 illustrate exemplary embodiments of an optical shape sensing device in accordance with the present invention.

As shown in FIG. 3, an optical shape sensing device 53 employs an elongated device 54 and a handle 55 for optical fiber 20. In this embodiment, six (6) degree-of-freedom markers 41 are embedded in handle 55, and the spatial relationship of reference markers 41 and reconstruction launch point 21 is known.

Figure 4:
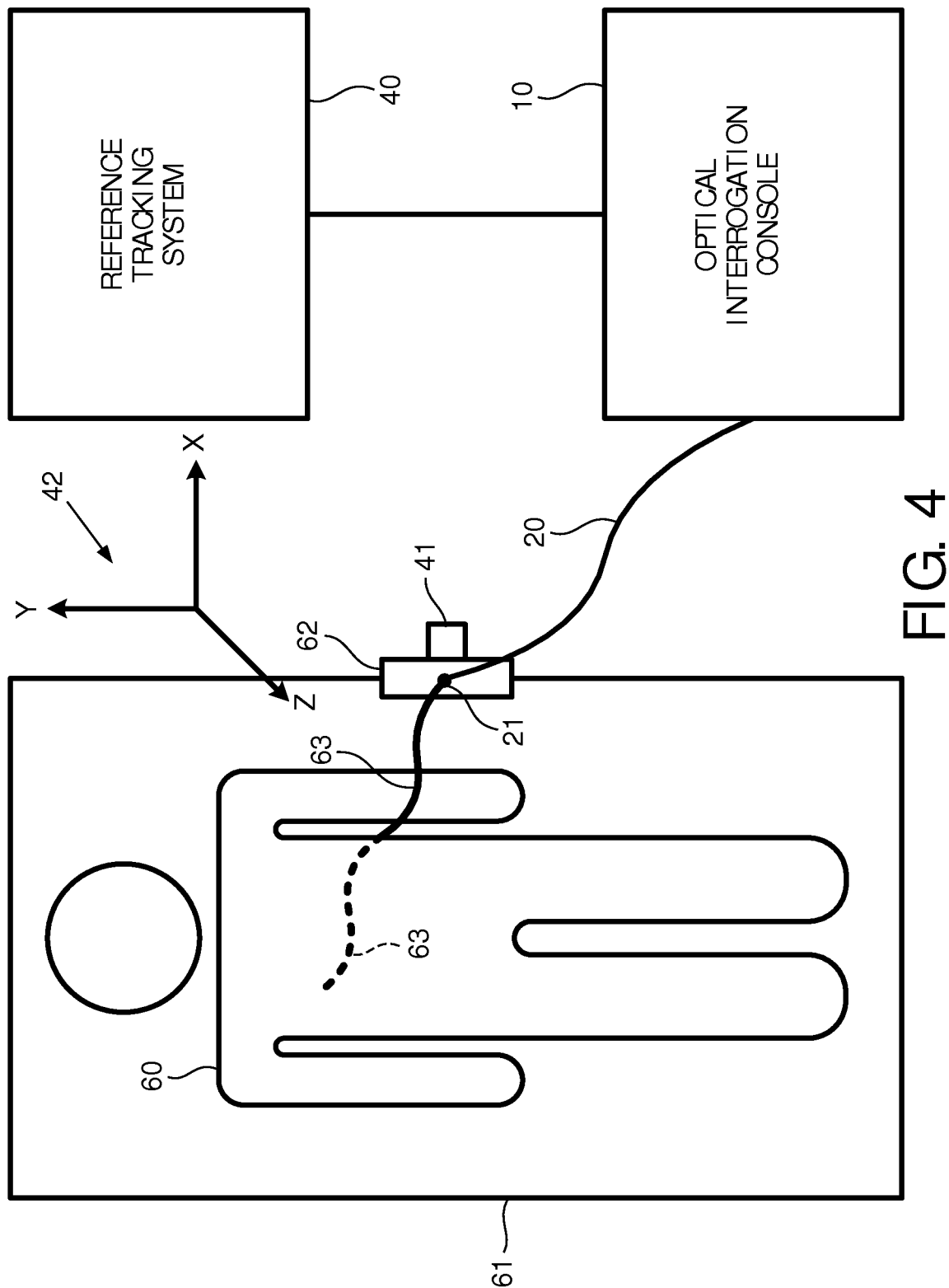

As shown in FIG. 4, an optical shape sensing device employs a platform 62 attached to an operating table 61 supporting a patient 60. In this embodiment, reference markers 41 are either affixed to or embedded within platform 62, and optical fiber 20 is embedded within an elongated device 63 at reconstruction launch point 21. In addition, the spatial relationship of reference marker 41 and reconstruction launch point 21 is known.

Figure 5:
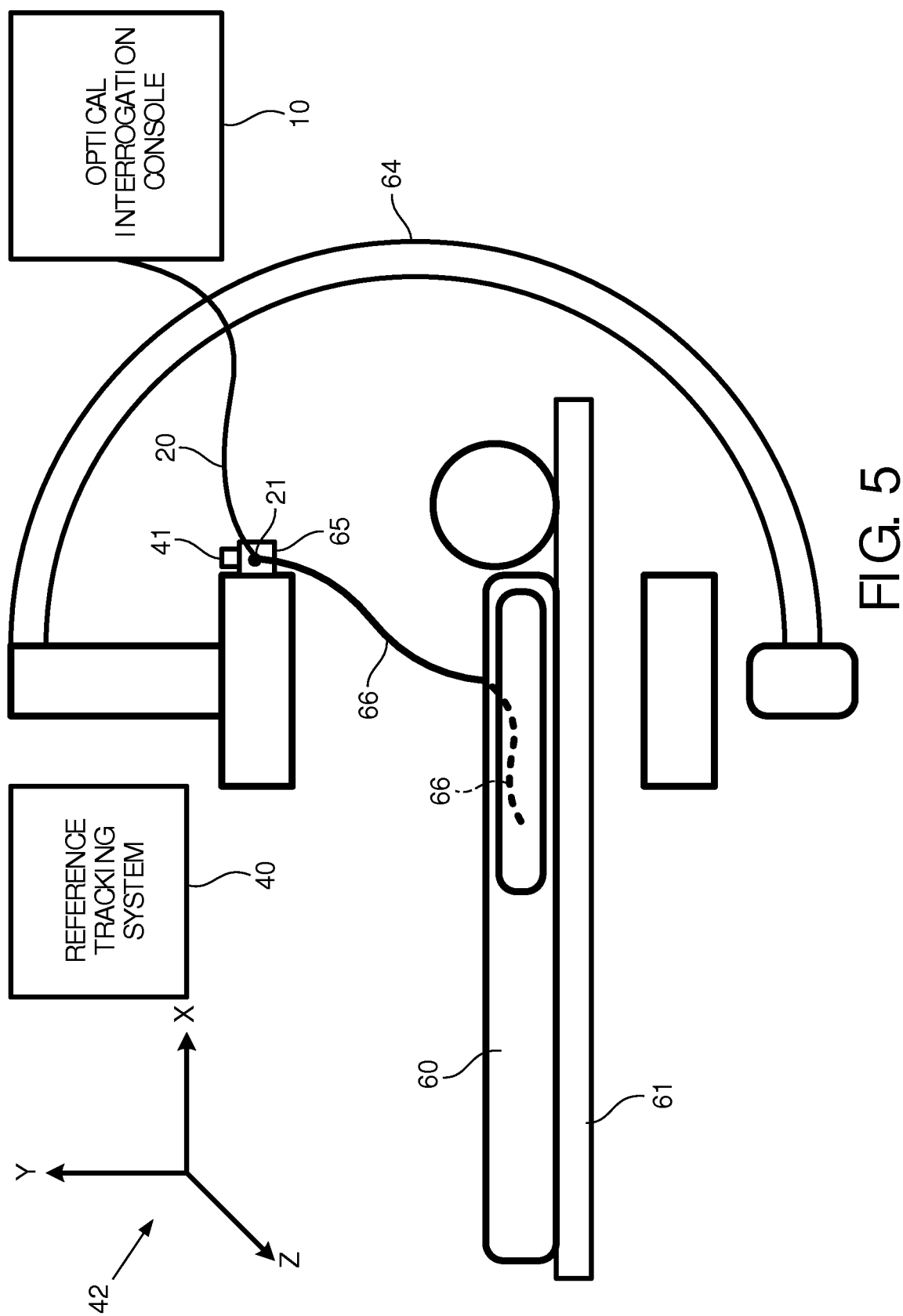

As shown in FIG. 5, an optical shape sensing device employs a platform 65 coupled to a C-Arm 64 of an X-ray system. In this embodiment, a reference marker 41 is affixed to platform 65, and optical fiber 20 is embedded within an elongated device 66 at reconstruction launch point 21. In addition, the spatial relationship of reference marker 41 and reconstruction launch point 21 is known.

From the description of FIGS. 1-5, those having ordinary skill in the art will have a further appreciation on how to manufacture and use an optical shape sensing system in accordance with the present invention for numerous surgical procedures.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. For example, although the invention is discussed herein with regard to FBGs, it is understood to include fiber optics for shape sensing or localization generally, including, for example, with or without the presence of FBGs or other optics, sensing or localization from detection of variation in one or more sections in a fiber using back scattering, optical fiber force sensing, fiber location sensors or Rayleigh scattering. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An optical shape sensing system, comprising:
   an elongated device;
   an optical fiber comprising a plurality of Bragg gratings and a reconstruction launch point in a reference coordinate system serving as a basis of a shape reconstruction of an entirety of the optical fiber, wherein at least a portion of the optical fiber is embedded within the elongated device;
   a reference marker having at least one of an identifiable reference tracking position and an identifiable reference tracking orientation within the reference coordinate system;
   a tracking system structurally configured to identify the at least one of the identifiable reference tracking position and the identifiable reference tracking orientation of the reference marker within the reference coordinate system,
      wherein the reconstruction launch point of the optical fiber has a known spatial relationship with the reference marker within the reference coordinate system, and
      wherein the tracking system is further configured to identify the reconstruction launch point within the reference coordinate system based on an identification by the tracking system of the at least one of the identifiable reference tracking position and the identifiable reference tracking orientation of the reference marker within the reference coordinate system; and
   an optical interrogation console structurally configured to reconstruct a shape of the entirety of the optical fiber within the reference coordinate system relative to the reconstruction launch point responsive to the identification by the tracking system of the reconstruction launch point within the reference coordinate system.

2. The optical shape sensing system of claim 1,
   wherein the tracking system is an electromagnetic reference tracking system for establishing the reference coordinate system, and
   wherein the reference marker is an electromagnetic reference marker.

3. The optical shape sensing system of claim 1,
   wherein the tracking system is an optical tracking system for establishing the reference coordinate system, and
   wherein the reference marker is an optical reference marker.

4. The optical shape sensing system of claim 1,
   wherein the tracking system is an imaging tracking system for establishing the reference coordinate system, and
   wherein the reference marker is identifiable within images generated by the imaging tracking system.

5. The optical shape sensing system of claim 1,
   wherein the known spatial relationship of the reconstruction launch point with the reference marker includes the reconstruction launch point being one of spaced from or coinciding with the reference marker within the reference coordinate system.

6. The optical shape sensing system of claim 1, further comprising:
   a handle coupled to the elongated device,
      wherein the reference marker is embedded with the handle.

7. The optical shape sensing system of claim 6, wherein the reconstruction launch point is fixed relative to the handle.

8. The optical shape sensing system of claim 1, further comprising:
   a platform,
      wherein the elongated device is coupled to the platform; and
      wherein the reference marker is one of affixed to or embedded within the platform.

9. The optical shape sensing system of claim 8, wherein the platform is attached to an operation table.

10. The optical shape sensing system of claim 8, wherein the platform is attached to an imaging system.

11. The optical shape sensing system of claim 8, wherein the reconstruction launch point is fixed relative to the platform.

12. The optical shape sensing system of claim 1, wherein the reconstruction launch point is adjacent an end of the optical fiber.

13. The optical shape sensing system of claim 1, wherein the reconstruction launch point is spaced from an end of the optical fiber.

14. The optical shape sensing system of claim 1,
   wherein an additional reconstruction launch point has a known spatial relationship with the reference marker within the reference coordinate system;
   wherein the tracking system is further configured to identify the additional reconstruction launch point within the reference coordinate system based on the identification by the tracking system of the at least one of the identifiable reference tracking position and the identifiable reference tracking orientation of the reference marker within the reference coordinate system; and
   wherein the optical interrogation console is further structurally configured to reconstruct the shape of the entirety or the segment of the optical fiber within the reference coordinate system relative to the additional reconstruction launch point responsive to the identification by the tracking system of the additional reconstruction launch point within the reference coordinate system.

15. An optical shape sensing method for an optical shape sensing system including an optical fiber and a reference marker, the optical shape sensing method comprising:
   providing at least a portion of the optical fiber embedded within an elongated device, the optical fiber comprising a plurality of Bragg gratings and a reconstruction launch point in a reference coordinate system serving as a basis of a shape reconstruction of an entirety of the optical fiber;
   identifying, via a tracking system, at least one of an identifiable reference tracking position and an identifiable reference tracking orientation for the reference marker within a reference coordinate system;

identifying, via the tracking system, the reconstruction launch point of the optical fiber within the reference coordinate system based on the identifying by the tracking system of the at least one of the identifiable reference tracking position and the identifiable reference tracking orientation for the reference marker within the reference coordinate system, wherein the reconstruction launch point has a known spatial relationship with the reference marker to enable the identification by the tracking system of the reconstruction launch point within the reference coordinate system; and reconstructing, via an optical interrogation console, the shape of the entirety of the optical fiber within the reference coordinate system relative to the reconstruction launch point responsive to the identification by the tracking system of the reconstruction launch point within the reference coordinate system.

16. The optical shape sensing method of claim 15, further comprising:

moving the reference marker and the optical fiber within the reference coordinate system while maintaining the known spatial relationship of the reconstruction launch point with the reference marker;

re-identifying, via the tracking system, the at least one of the identifiable reference tracking position and the identifiable reference tracking orientation for the reference marker within the reference coordinate system;

re-identifying, via the tracking system, the reconstruction launch point of the optical fiber within the reference coordinate system based on the re-identifying by the tracking system of the at least one of the identifiable reference tracking position and the identifiable reference tracking orientation for the reference marker within the reference coordinate system; and reconstructing, via the optical interrogation console, the shape of the entirety of the optical fiber within the reference coordinate system relative to the reconstruction launch point responsive to the re-identification by the tracking system of the reconstruction launch point within the reference coordinate system.

17. The optical shape sensing method of claim 15, further comprising:

sensing, via the tracking system, a movement of at least one of the optical fiber and the reference marker within the reference coordinate system subsequent to the identification of the reconstruction launch point by the tracking system within the reference coordinate system; and providing, via the tracking system, feedback indicative of the sensed movement of at least one of the optical fiber and the reference marker within the reference coordinate system.

18. The optical shape sensing method of claim 15, further comprising:

selecting, via the optical interrogation console, the reconstruction launch point from a plurality of reconstruction launch points prior to the identification of the reconstruction launch point by the tracking system within the reference coordinate system.

19. The optical shape sensing method of claim 18, further comprising:

providing a display of the plurality of reconstruction launch points to enable the selection of the reconstruction launch point from the plurality of reconstruction launch points.

* * * * *